US008158241B2

(12) United States Patent
Reilly et al.

(10) Patent No.: US 8,158,241 B2
(45) Date of Patent: Apr. 17, 2012

(54) ARTICLE DISPLAYING EDGEWISE, ANGULAR MULTI-CHROMATIC CHARACTERISTICS

(75) Inventors: Jack J. Reilly, Blue Bell, PA (US); Douglas R. Dillon, Norristown, PA (US)

(73) Assignee: Arkema France, Colombes (FR)

( * ) Notice: Subject to any disclaimer, the term of this patent is extended or adjusted under 35 U.S.C. 154(b) by 1316 days.

(21) Appl. No.: 10/776,884

(22) Filed: Feb. 11, 2004

(65) Prior Publication Data

US 2004/0191492 A1 Sep. 30, 2004

Related U.S. Application Data

(60) Provisional application No. 60/451,901, filed on Mar. 4, 2003.

(51) Int. Cl.
*B32B 7/02* (2006.01)

(52) U.S. Cl. .......... 428/212; 428/220; 428/38; 428/192; 428/207; 428/542.2

(58) Field of Classification Search .................... 428/38, 428/172, 192, 195.1, 207, 212, 542.2, 204
See application file for complete search history.

(56) References Cited

U.S. PATENT DOCUMENTS

| 3,264,164 | A | | 8/1966 | Jerothe | |
| 3,853,675 | A | | 12/1974 | Edwards | |
| 3,940,523 | A | | 2/1976 | Lecoeure et al. | |
| 4,298,217 | A | | 11/1981 | Moraw | |
| 4,469,725 | A | | 9/1984 | Fischer | |
| 4,626,454 | A | | 12/1986 | Sandman | |
| 4,877,077 | A | | 10/1989 | Ebert | 160/236 |
| 5,585,425 | A | * | 12/1996 | Kito et al. | 524/324 |
| 5,622,259 | A | * | 4/1997 | Church | 206/363 |
| 5,772,827 | A | | 6/1998 | Malm | 156/244.11 |
| 5,915,549 | A | * | 6/1999 | Palmer et al. | 206/308.1 |
| 6,103,161 | A | | 8/2000 | Lopez | 264/148 |
| 6,103,345 | A | | 8/2000 | Oshima | 428/172 |
| 6,465,101 | B1 | | 10/2002 | MacGregor et al. | 428/412 |
| 6,486,251 | B1 | | 11/2002 | Patel | 524/439 |

FOREIGN PATENT DOCUMENTS

| BE | 1009861 | 10/1997 |
| EP | 0215324 | 8/1986 |

OTHER PUBLICATIONS http://hyperphysics.phy-astr.gsu.edu/hbase/tables/indrf.html, 1999, Carl Nave.*

* cited by examiner

*Primary Examiner* — David Sample
*Assistant Examiner* — Lawrence Ferguson
(74) *Attorney, Agent, or Firm* — Thomas F. Roland (57) ABSTRACT

The present invention is directed to an article of manufacture having differently colored layers which, when viewed from the edge, change color depending on the angle of view. The articles can be used in decorative or eye-catching displays suitable for displaying information or promoting objects.

31 Claims, 2 Drawing Sheets

ARTICLE DISPLAYING EDGEWISE, ANGULAR MULTI-CHROMATIC CHARACTERISTICS

REFERENCE TO RELATED APPLICATIONS

This application claims priority of U.S. Provisional Application 60/451,901 filed Mar. 4, 2003.

BACKGROUND OF THE INVENTION

1. Field of the Invention

The present invention pertains to materials and articles of manufacture having a decorative or artistic appearance. The present invention also relates to materials or articles having interesting or attractive appearances that can be used, for example, in decorative applications or serve in a display, sign, or consumer product.

2. Discussion of Prior Art

The promotion or advertisement of goods and services often utilizes eye-catching displays or signs designed to attract consumers and single out products from among numerous others. Materials used in eye-catching displays or signs are widely variable, but often involve numerous color combinations and sometimes special optical effects. Plastics and related materials have been materials of choice for their versatility, offering an essentially infinite variety of color, shapes, sizes, and other desirable properties such as rigidity or flexibility.

Some examples of plastic materials allowing numerous color variation and optical effects through layering and other techniques are mentioned below. U.S. Pat. No. 3,940,523 reports layered acrylic articles incorporating horizontal and vertical barriers within the layers to prevent colored areas from mixing. U.S. Pat. No. 4,877,077 is directed to a multi-layered coextruded slat of thermoplastic polymer having an opaque layer, a transparent pearlescent layer, and an optional intermediate transparent colored layer. U.S. Pat. No. 5,772,827 reports a method for making a plastic trim strip, such as for a car, having an opaque base layer, a transparent upper layer, and an intermediate bright or colored layer. U.S. Pat. No. 6,103,161 reports a method and apparatus for making a three-layered thermoplastic article having a white base layer, a striped intermediate layer, and a transparent upper layer. U.S. Pat. No. 6,103,345 is directed to a decorative sheet having front and rear surfaces with parallel striped patterns with predetermined pitches to produce a changeable color effect with the angle of observation. Further, U.S. Pat. No. 6,465,101 is directed to a multilayered plastic article having a base layer and at least one protective surface layer or film and optional decorative intermediate layers. U.S. Pat. No. 6,486,251 reports impact resistant polycarbonate/polyester resin incorporating colored flakes that preferably impart optical effects such as pearlescence, metallic sparkle, metallic luster, or angular metamerism.

As is evident from the literature described above, materials that have enhanced visual appeal are in constant demand. For example, manufacturers need new and better methods for drawing consumers to their products and increasing brand awareness. Further, manufacturers desire new ways in which to enhance their products decoratively to make them more appealing. Thus, there is an ongoing need to find new and different ways in which to make products stand out. The articles and methods described hereinbelow help fulfill these and other needs.

SUMMARY OF THE INVENTION

The present invention is directed to an article comprising two or more layers, where each of the layers has a principal color and one or more of the layers is light transmitting. The article can have at least one edge that exposes at least one light transmitting layer. The observed color of the at least one exposed light transmitting layer, when viewed along said edge, can appear different than its principal color. In some embodiments, the observed color of the at least one exposed light transmitting layer, when viewed along said edge, changes with respect to viewing angle, such as at one or more threshold viewing angles. Additionally, the observed color of the at least one exposed light transmitting layer, when viewed along the edge, can appear to have color contributions from two or more principal colors.

Articles of the present invention can, for example, have three or more layers. According to some embodiments, two or more layers can be light transmitting or all of the layers are light transmitting. In further embodiments at least one of the layers is opaque or translucent.

Additionally, articles of the present invention can have two or more layers of plastic or glass. In some embodiments, plastic layers contain acrylic polymer such as polymethyl methacrylate. In further embodiments, article layers are made of substantially the same material.

Articles of the present invention can further have at least two adjacent light transmitting layers. In some embodiments, the indices of refraction of adjacent layers are substantially the same. In further embodiments, the indices of refraction of adjacent layers are within about 0.5 of each other. In yet further embodiments, the layers have indices of refraction greater than air or at least about 1.05.

According to further embodiments, articles can have a depth measured from the edge wherein the depth is variable. Depth can be varied, for example, by cuts through the layers.

In yet further embodiments, articles can contain an interlayer material. The interlayer material can be a liquid or a plastic having an index of refraction between about 1.05 and about 2.0.

Articles of the present invention further include those having two or more layers that are light transmitting acrylic polymers having indices of refraction of at least about 1.05 and within about 0.5 of each other, wherein the two or more layers are coextruded.

Articles of the present invention further include those having two or more layers that are light transmitting acrylic polymers having indices of refraction of at least about 1.05 and within about 0.5 of each other, wherein the two or more layers are separated by an interlayer having a lower index of refraction than the two or more layers. The interlayer can be a liquid or a plastic having, for example, an index of refraction that is lower by about 0.1 or less.

Further embodiments include articles in the form of a sheet or sheet that is transformed into a three-dimensional form. The three-dimensional form can be suitable for a display, consumer product, or decorative support for an object.

The present invention is further directed to a method of displaying an object comprising supporting the object with an article of the present invention.

DESCRIPTION OF PREFERRED EMBODIMENTS

The present invention is directed to, inter alia, articles that have a surprising optical effect derived from penetration of light through one or more layers of differently colored materials. The optical effect can be referred to as "angular multi-chromatic characteristics" or "geometric multi-chromatic characteristics" in which observed color (i.e., the color actually perceived at any point in time) is dependent on viewing angle. For example, an object showing angular multi-chromatic characteristics can appear to change color solely based on observation at different angles. The articles of the present invention can show changing coloration along one or more of its edges, thus exhibiting what can be called "edgewise, angular multi-chromatic characteristics."

The present articles can include two or more layers of any suitable material. The materials can be the same or different for individual layers. Suitable materials include glass, quartz, plastics, or any other material that can refract light. In some embodiments, articles can contain three, four, or even five layers. In some embodiments, articles are in the form of layered sheets.

Example materials suitable as layers in the present invention include thermoplastics such as, but not limited to, polycarbonate, polyethylene terephthalate-glycol modified, polyvinyl chloride, impact modified polyvinyl chloride, polyesters, cyclic olefin copolymers, styrene acrylonitrile, acrylonitrile-styrene-acrylate terpolymer, acrylonitrile butadiene styrene terpolymer, imidized acrylic polymer, acrylic polymers or impact modified acrylic polymers. Other suitable polymers can include allyl diglycol carbonate (CR-39®), fluoropolymers such as Teflon® and polyvinylidene fluoride (PVdF), mixtures thereof, acrylic blends thereof, acrylic copolymers thereof, and the like.

Acrylic polymers can include alkyl methacrylate homopolymers, copolymers of alkyl methacrylates with other alkyl methacrylates or alkyl acrylates or other ethylenically unsaturated monomers, alkyl acrylate homopolymers, and copolymers of alkyl acrylates with other alkyl acrylates or alkyl methacrylates or other ethylenically unsaturated monomers. Alkyl groups can be straight-chain, branched, or cyclic and can have from 1 to about 18, preferably 1 to about 8, or more preferably 1 to about 4 carbon atoms. In some embodiments, layers include polymers of methyl methacrylate or copolymers thereof. Copolymers of methyl methacrylate can include alkyl acrylates (e.g., in an amount of about 0.1 to about 99 wt % or about 0.1 to about 20 wt %) such as methyl acrylate or ethyl acrylate and optionally alkyl acrylic acids. Layers can be prepared by any suitable method known in the art such as by cell casting, casting or melt processing techniques.

Thermoplastic layers can further include modifiers or additives known in the art. For example, thermoplastics can contain impact modifiers, antioxidants, flame retardants, ultraviolet stabilizers, flow aids, anti-static agents, lubricants, light-diffusing particles, gloss-controlling particles, colorants, special effect particles such as mica or metal flakes, and the like.

Each of the layers is characterized by a principal color which is the color of the layer due to, for example, a dye or pigment within the layer. The principal color of a layer can be observed, for example, through the layer thickness when the layer is alone or combined with colorless materials. The principal color of a layer can also be measured spectrally by an absorption or transmission spectrum. Acquisition of absorption and transmission spectra are routine in the art. According to some embodiments, each layer has a different principal color. In some embodiments, adjacent layers have different colors or different shades of a color within the same hue. Any color is suitable as a principal color including all colors within the visible range of the electromagnetic spectrum. The principal color of a layer can also appear colorless, such as for materials having only weak or no spectral signals (e.g., no absorption bands or transmission peaks) in the visible spectrum. In some instances, colorless layers can include tints or toners, such as for making the edge appear neutral. Dyes or pigments in the layers can further have fluorescent, phosphorescent, electrochromic, photochromic, pearlescent, effervescent, or other special effect properties.

In articles of the present invention, one or more of the layers is light transmitting. Light transmitting layers are transparent, allowing, for example, objects or images to be clearly perceived through the layer. Light transmitting layers can have a measurable luminous transmission greater than about 0% and a haze value less than about 30%. Typically colorless light transmitting layers have a luminous transmission greater than about 60%. Other layers can be translucent or opaque. Translucent layers admit and diffuse light such that objects or images usually cannot be clearly perceived through the layer. Translucent layers typically have a measurable luminous transmission greater than about 0% and a haze value of more than about 30%. Opaque layers typically do not allow light to penetrate entirely through, and have a luminous transmission of about 0%. Luminous transmission and haze can be measured by any method known in the art such as according to ASTM D 1003 or techniques described in the Examples.

In some embodiments, articles have one, two, three, four, or more light transmitting layers. Light transmitting layers can be adjacent to one another or separated by one or more translucent or opaque layers. In some embodiments, articles can comprise only light transmitting layers. Any combination of one or more light transmitting layers and opaque or translucent layers is also suitable.

Individual layers of the present articles can have the same or different thicknesses. Suitable layer thickness can range, for example, from about 0.001 to about 100 mm, about 0.01 to about 20 mm, about 0.1 mm to about 20 mm, or about 1 mm to about 12 mm. In further embodiments, the thickest layer is a light transmitting layer. In some embodiments, the thickness of a light transmitting layers can range from about 0.2 mm to about 50 mm, about 1 mm to about 15 mm, or about 2 to about 12 mm. Layers can have a uniform thickness throughout the article.

Opaque and translucent layers can be formed by any suitable material capable of imparting translucency or opaqueness. In addition to pigmented glasses and plastics, example opaque layers can be one or more layers of paint, foil, metal, paper, cardboard, or combinations thereof. Example translucent layers include many commercially available translucent plastics (Plexiglas® MC sheet in the following colors: 2157 Red, 2108 Green, 2114 Blue, for example, Plexiglas® G or MC sheet in W7328 White, Plexiglas® Frosted sheet products, etc.) or frosted glass.

Figure 1:
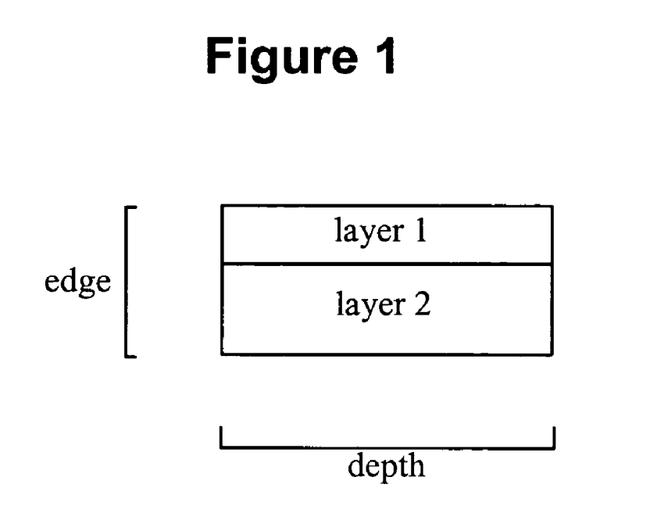
FIG. 1 shows a side view of an example 2-layer article of the present invention.

Articles of the invention have at least one edge that exposes the material of at least one light transmitting layer. An edge can also expose more than one layer material, and in some embodiments, can expose all the layer materials. Edges can be, for example, straight (i.e., perpendicular to the surface of the article, see FIG. 1) or wholly or partially beveled (i.e., at an angle to the surface of the article). Accordingly, one or more layers can be seen from an edge-on view of the article. Typically, layers can be flush with one another along the edge.

According to the present invention, angular multi-chromatic characteristics can be observed along the edge of the article. For example, when an observer views the edge at a first angle, each of the principal colors of one or more exposed light transmitting layers can be perceived along the edge. When the observer views the edge from a second angle, the one or more light transmitting layers can appear to have a color different from its principal color. This angular multi-chromatic effect can be observed, for example, by rotating an article from an edge-on view to a full surface view. As the edge rotates away (or toward) an observer, the perceived edge color can change.

The change of color along the edge can involve an initial observation of the principal colors of each of the edge-exposed layers followed by subsequent replacement of the principal color of at least one light transmitting layer with another color, after changing angle of view. The newly observed color can, in some embodiments, appear to be a mixture of two or more principal colors from any light transmitting, translucent, or opaque layer.

Any method for measuring color known in the art can be used to detect the difference between a principal color and a newly observed color due to the angular multi-chromatic effect. Images of the edge of an article can be acquired (such as by color photography, conventional or digital) and the colors displayed therein measured and compared. For example, with digital images, RGB values can be compared, or with any image, color index coordinates according to CIE (Commission Internationale de l'Eclairage) can be compared. Additionally, color measured from images can be color-matched against, for example, standard samples to determine color change due to the angular multi-chromatic effect.

Figure 3:
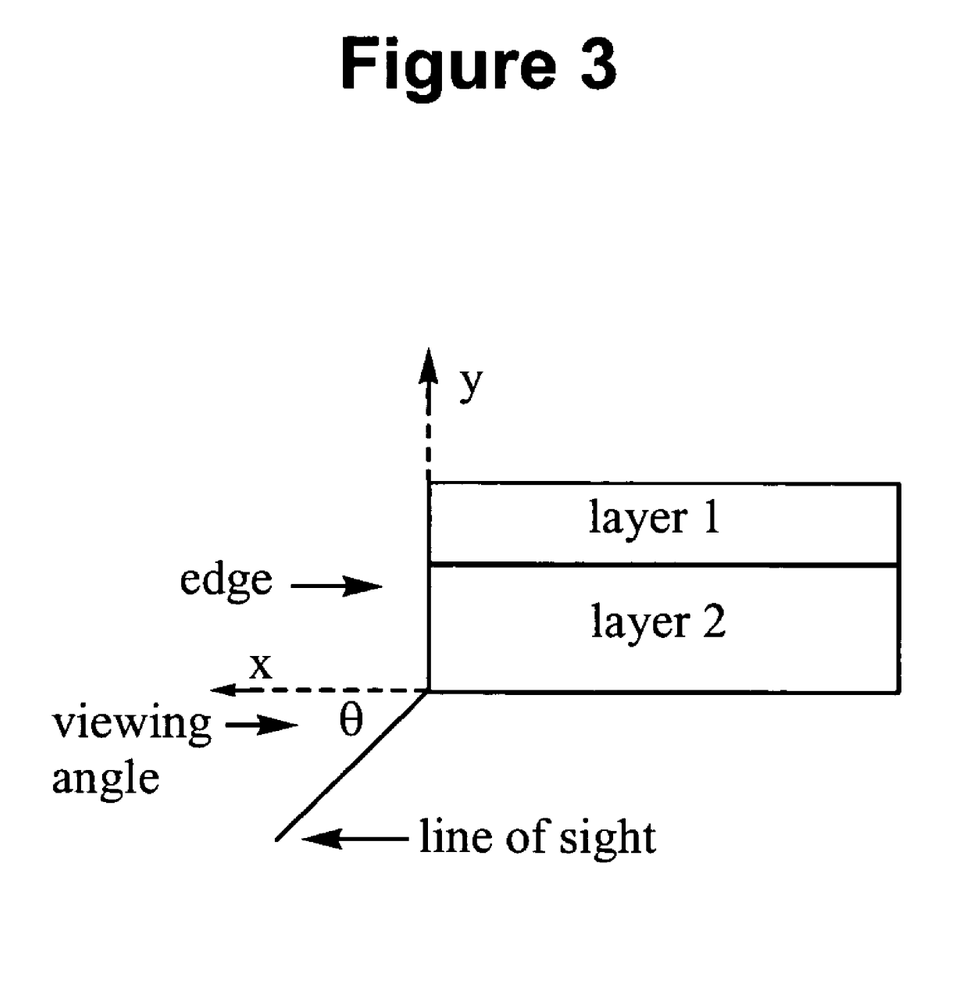
FIG. 3 shows a side view of an example 2-layer article of the present invention in relation to an arbitrary line of sight showing an example angle of view.

The angle of view (viewing angle) can describe all positions in which an observer can see the edge of an article. Accordingly, the angle of view can be measured from the line of sight to the surface of any desired layer. The angle of view has an angular component within a plane perpendicular to plane containing the edge and the plane containing the layer surface. See, for example, FIG. 3 where an example angle of view □ (viewing angle) in an x,y-plane is illustrated. According to FIG. 3, a viewing angle of 0° would include looking at the article edge-on (e.g., along the x-axis in FIG. 3), whereas a viewing angle of 90° (e.g., looking along the y-axis in FIG. 3) might result in an inability to see the edge surface. Angles of view can also have a z-axis component.

In some embodiments, the edgewise, angular multi-chromatic effect (i.e., observed color change on the edge) occurs at a threshold viewing angle ($\Box_t$) or a range of threshold viewing angles. In an example scenario, an observer looking edge-on (e.g., □ is 0°) can perceive each of the principal colors of the exposed layers on the edge of the article. As the article is rotated toward, for example, a viewing angle of 90°, at some point during the rotation the observer can perceive a color change along the edge in at least one light transmitting layer. In accordance with this example scenario, the threshold viewing angle ($\Box_t$) (or range of angles) would occur between 0° and 90°, at an angle (or range of angles) during which the color change was observed. Similarly, threshold viewing angles can often be determined for the other direction, i.e., rotating the article 0° to −90°, and may be asymmetrical. The two threshold viewing angles can define a "principal color viewing width" which is the distance between the two threshold viewing angles at a preselected distance from the edge of the article.

The edgewise, angular multi-chromatic effect observed in articles of the present invention can be thought to be the result of certain optical effects. While not wishing to be bound by theory, it is believed that when an observer perceives each of the principal colors along the edge, the observer is seeing the result of either, or a combination of, total internal reflection within each of the layers or light transmitted through the depth of the layers (e.g. seeing edgewise through the article), resulting in observation of distinct colors of individual layers. When the observer perceives a color along the edge that does not correspond to a layer's principal color, the observer sees the result of color contributions from two or more layers. Whether the observer sees principal colors or other colors depends on the wavelength of light reflected, transmitted, or refracted from the edge which is, in turn, dependent on the angle of view. Thus, above or below certain threshold viewing angles, an observer will either see the result of total internal reflection and/or light transmitted through the individual light transmitting layers (i.e., observation of principal color) or see the result of color contributions from more than one layer where total internal reflection within individual light transmitting layers is reduced or not optically available at the angle of view.

Figure 2:
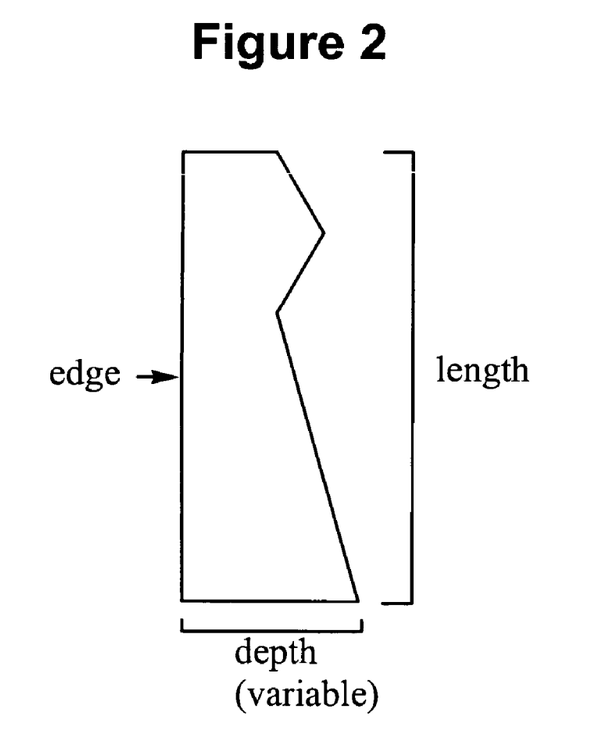
FIG. 2 shows a surface view of an example article of the present invention having variable depth.

Threshold viewing angle can be controlled by several different parameters associated with an article of the present invention. For example, threshold viewing angle can be controlled by modifying the depth of the article (see, e.g., FIGS. 1 and 2). Depth can be described as the distance between the edge and an opposite edge or side of an article. Decreasing depth can increase threshold viewing angle thereby allowing a greater principal color viewing width (and, consequently, a narrower range for observing colors other than the principal colors). Conversely, increasing depth can decrease the threshold viewing angle resulting in a narrower principal color viewing width. This effect is most readily observed when the layers all have the same refractive index.

Modification of article depth can be accomplished according to any suitable method. According to some embodiments, depth can be varied to impart a range of threshold angles along the edge of an article of the invention. In this way, articles can be irregularly shaped (see, e.g., FIG. 2) or can be cut to any desirable shape so that depth varies between the edge where the angular multi-chromatic effect is observed and an opposite side or edge. In another embodiment, cuts or cut-outs can be made through (or partially through) the thickness of the article to effectively decrease the depth in one or more areas while leaving the majority of the object intact. Cuts can be made by any appropriate means such as by laser cutting.

Threshold viewing angle can also be controlled by modifying the thickness of the light transmitting layers. Increasing the thickness of one or more light transmitting layers can increase the threshold angle allowing a greater principal color viewing width. Conversely, decreasing thickness of one or more light transmitting layers can decrease threshold angle allowing a narrower principal color viewing width.

Threshold angle can also be controlled by modifying the index of refraction of the light transmitting layers. Higher indices of refraction can result in greater threshold angles, thereby broadening the principal color viewing width. Lower indices of refraction can have the opposite effect, resulting in a narrower principal color viewing width. Index of refraction can be modified by selecting appropriate materials to comprise the layers of the article. Index of refraction can be measured by methods well known in the art such as according to ASTM D 542. Suitable indices of refraction include, for example, at least about 1.05, at least about 1.1, at least about 1.2, at least about 1.3, or between about 1.05 and about 2.0, between about 1.1 and about 1.8, and between about 1.1 and about 1.7.

Threshold viewing angle can also be controlled by differences in refractive index between layers. Articles having layers of different refractive indices can have threshold angles that show reduced dependence on depth or are independent of article depth. In some embodiments, articles can have at least one layer that has a lower refractive index than adjacent layers. Larger differences in refractive index between adjacent layers can result in increased threshold viewing angle and increased principal color viewing width. According to some embodiments, difference in refractive index between adjacent layers can be selected such that a threshold viewing angle is observable, for example, occurring at a viewing angle less than about 90°. Beyond about 90°, the multi-chromatic effect would likely be difficult to detect in some embodiments because the edge could not be observed. According to some embodiments, the indices of refraction of adjacent layers can have differences of about 0.5 or less, about 0.4 or less, about 0.3 or less, about 0.2 or less, or about 0.1 or less. In some embodiments, the difference in index of refraction for individual layers is about 0, such as for articles having layers of the same material.

According to the present invention, the layers of the article can be in optical contact. The term "optical contact" is used herein in accordance with the art and typically means that there is a single optical boundary between adjacent layers or essentially no optical boundary between layers (such as for fused layers of the same material). For example, stacked separate sheets of transparent plastic or other materials are not in optical contact with each other, but are in optical contact with an intervening film of air between the sheets. In contrast, layers of a thermoplastic material which are fused by, for example, melting, fusion bonding, or coextrusion are in optical contact.

In some embodiments, layers are in optical contact with an interlayer material that can be inserted between layers. Interlayer material can be a liquid or a solid layer or film having the same or different index of refraction of adjacent layers. The difference in index of refraction between interlayer material and an adjacent layer can be about 0.5 or less, 0.4 or less, 0.3 or less, 0.2 or less, 0.1 or less, or about 0. As with any of the other layers in the article of the invention, difference in refractive index between an interlayer and adjacent layers can be selected such that a threshold viewing angle is observable, such as for a viewing angle less than about 90°. Beyond about 90°, the multi-chromatic effect would likely be difficult to detect in some embodiments because the edge cannot be observed. Smaller differences in refractive index of interlayer material and adjacent layers are more likely to result in observable threshold angles and, therefore, an observable, angular multi-chromatic effect.

Some interlayer materials include, for example, liquids, such as water, glycerol, oils (e.g., petroleum-based oils, mineral oil, animal- or vegetable-based oils), greases, gels, and the like. Other interlayer materials include solids or hardening liquids such as polymers, glues, epoxies, cements, polymerizing solutions, and the like. Some solid interlayer materials include, for example, polyurethane, polyvinybutyrate, mixtures thereof, acrylic blends thereof, acrylic copolymers thereof, and the like. Interlayers can be colored or coloress.

Optically contacted layers further include fused layers such as can be prepared by any appropriate method including, for example, melting, fusion bonding, calendaring/lamination, film lamination, film insert molding, co-injection molding, multi-shot molding, insert molding or coextrusion. Methods for using each of the above processing techniques on thermoplastics to form layered articles are well known in the art.

An article of the present invention can be made by any suitable method in the art for preparing layers in optical contact. As an example, preformed layers, such as differently colored plastic sheets formed by cell casting or other methods can be treated or coated with an interlayer material such as a liquid and then assembled by stacking the sheets such that the interlayer material is dispersed evenly between each of the layers. The layers can be physically held together by clamps or other similar means or the interlayer material can further serve as an adhesive or bonding agent that effectively holds the assembled stack together, such as in autoclave lamination techniques.

Articles of the present invention can further be made by coextrusion of differently colored thermoplastic materials with two or more extruders that convert plastic resin materials into molten plastic in separate streams. The streams can be combined, for example, in a feedblock system or in a multi-manifold die set-up to form a thermoplastic sheet with two or more differently colored layers. Parameters for operating a coextrusion system are known in the art.

Edges can be formed according to any suitable technique. For example, in connection the assembly method, edges of each of the individual sheets can be aligned so that they are flush with one another, at least along one side, to form an edge where the angular multi-chromatic effect can be observed. Optionally, the assembled stack or coextruded product can be cut using, for example, a laser to produce such an edge. The edge could alternatively be cut with a saw or router and subsequently edge finished, flame polished, further polished, buffed, sanded, or smoothed to reduce light scattering and enhance any multi-chromatic effect observed.

Articles of the present invention can, for example, take the form of a layered sheet, such as can be formed by two or more layers. Sheets can have a thickness of from about 1 mm to about 500 mm. The sheet can be transformed, such as, cut, bent, molded, fabricated, thermoformed, heat bent, shaped, cemented, etched, engraved, drilled, mechanically or chemically or physically fastened, flame polished, sanded, or buffed to into any three-dimensional shape. The transformed sheet typically retains at least one edge that shows an angular multi-chromatic effect. Techniques for the transformation of materials such as glass and plastic to form preselected three-dimensional forms are well known in the art.

In some embodiments, the article can be used for a display, consumer product, or a decorative support for an object. Accordingly, the present invention further includes methods of displaying an object by supporting the object with articles of the present invention.

Articles of the present invention can have any number of uses including, for example, advertising, increasing brand-awareness, and attracting consumers. Decorative uses can include rendering objects or products more appealing to consumers or viewers. Thus, articles can be used for displays, consumer products, or decorative supports for one or more objects. Accordingly, the present invention further includes methods of displaying an object by supporting the object with an article of the present invention. Articles can also be useful for displaying information.

Suitable displays, consumer products, or decorative supports include those that typically contain glass or plastic and/or are intended for viewing in lighted conditions (e.g., natural or artificial lighting, or under conditions where one or more of the edges are illuminated). Example displays, consumer products, or decorative supports include, display cases, point-of-purchase displays, shelving, risers, frames, signs, signs that rotate, shields, trinkets, keepsakes, memorabilia, artwork, sculpture, glazing, fountains, vases, furniture, tableware, and the like. Example displays or supports can be suitable for any consumer product such as cosmetics, clothing, shoes, and the like. Displays, consumer products, or supports can be made such that the edgewise, angular multi-chromatic effect is visible to observers (such as consumers) who are likely to view objects supported by the displays or supports. In some embodiments, the edge or edges showing an angular multi-chromatic effect, or portions of such edges, are oriented vertically or horizontally, such that a passerby could observe a color change as they move past or approach the display. In embodiments where the display, consumer product, or support includes articles of the present invention having variable depth, a passerby can observe variable color change on the edge where different portions of the edge change color at different times as the viewing angle changes. Thus, the articles of the present invention can be more eye-catching and attractive than conventional colored display means due to the edgewise, angular multi-chromatic effect.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety. In order that the invention disclosed herein may be more efficiently understood, examples are provided below. It should be understood that these examples are for illustrative purposes only and are not to be construed as limiting the invention in any manner.

EXAMPLES

Example 1

Comparative Article

Monolithic sheet samples of 0.118" thick, Plexiglas® MC 3152 Fluorescent Blue and Plexiglas® MC 3190 Fluorescent Green were each melt processed on a sheet extrusion line. These samples are commercially available from ATOFINA Chemicals, Inc. (Atoglas Division in North America). The refractive index of the resin matrix used in the Plexiglas® MC sheet color formulations is 1.492 as measured in conformance with ASTM D 542. Samples of each of the 2 colors were cut to size (about 3"×4"). The sample edges were subsequently finished using an Edge Finisher Company, Model #EF-200 edge finisher equipped with a diamond bit.

Optical measurements were made on the individual samples using a MacBeth® Color-Eye® 7000 spectrophotometer (Division of Kollmorgen Instruments Corporation), Illuminant C and the 2° standard observer. The equipment was calibrated in transmission mode using barium sulfate standard. Luminous transmission (CIE tristimulus Y value) and the CIE tristimulus color values (L*, a*, and b*) were calculated in conformance with ASTM E 308. Haze values were measured in conformance with ASTM D 1003. The transmission, haze and transmitted color properties are summarized below in Table I.

TABLE I

Optical Properties of Monolithic Fluorescent Sheet Colors

| Sample | Thickness (inches) | Transmission (%) | Haze (%) | Transmitted Color L* | a* | b* |
|---|---|---|---|---|---|---|
| 3152 Blue-1 | 0.118 | 90.9 | 0.9 | 96.4 | 0.35 | −1.92 |
| 3190 Green | 0.119 | 91.8 | 2.9 | 96.7 | −16.1 | 42.9 |
| 3152 Blue-2 | 0.118 | 91.0 | 1.0 | 96.4 | 0.34 | −1.91 |

Two samples of 0.118" thick, Plexiglas® MC 3152 Fluorescent Blue were used to sandwich a 0.118" thick sample of 3190 Fluorescent Green (edge color looks yellow-green). The resultant 3-layered acrylic sample was then clamped to hold the layers together. The edgewise, angular multi-chromatic effect was not observed in this article.

Example 2

Article of the Present Invention

This article was prepared as in Example 1 except that glycerol was applied to each side of the 3190 Green sample prior to sandwiching it between the 3152 Blue samples. The Glycerol used in this study is commercially available (Catalog #13,487-2, Chemical Abstracts Service Registry Number 56-81-5) from Aldrich Chemical Company, Inc. The manufacturer reported a measured refractive index value of 1.473 on a sample taken from the same lot that we used in our testing. The resultant 5-layer sample (3 layers of acrylic plus 2 layers of glycerol) was then clamped together to minimize the thickness of each of the glycerol contact layers. The optical and color properties of the multi-layer samples from Examples 1 and 2 are summarized below in Table II.

TABLE II

Optical Properties of Multi-Layer Fluorescent Sheet Colors

| Sample | Thickness (inches) | Transmission (%) | Haze (%) | Transmitted Color L* | a* | b* |
|---|---|---|---|---|---|---|
| Example 1 | 0.354 | 76.3 | 4.2 | 90.0 | −15.6 | 39.9 |
| Example 2 | 0.355 | 88.0 | 2.7 | 95.2 | −16.6 | 42.2 |

In Example 1, the transmission value is lower primarily due to the reflection losses at the acrylic/air/acrylic interfaces between acrylic layers 1 and 2, and between acrylic layers 2 and 3. The glycerol was used in Example 2 to make optical contact between the acrylic layers. Also, since the refractive index of glycerol (1.473) is much closer to that of the Plexiglas® MC sheet (1.492) than the refractive index of air (1.000) is to the acrylic sheet, the above reflection losses between the acrylic layers are significantly reduced. Therefore, a higher transmission value is achieved in the 5-layer sample of Example 2.

Additionally, when looking directly through the edge of the Example 1 sample (e.g. θ=0°), the 2 blue surface layers and the yellow-green middle layer are each visible. The edge color of each layer is distinctly separate from the adjacent layer(s). As the viewing angle is incrementally increased to one approaching 90°, the edge color of each layer still remains separate from the edge color of each of the adjacent layer(s). No angular multi-chromatic effect is observed.

When looking directly through the edges of the Example 2 sample (e.g. θ=0°), the 2 blue surface layers and the yellow-green middle layer are each visible and separate as in Example 1. However, as the viewing angle is incrementally increased, the edge colors of each of the layers change to a similar color (greenish—with color contributions from each of the 3 light-transmitting acrylic layers) at a threshold viewing angle. The Example 2 sample exhibits an edgewise, angular multi-chromatic effect when viewing the 5-layer construction from the edges. Note that the threshold viewing angle is about the same when viewing through the 3" or 4" path lengths.

Example 3

Comparative

Monolithic sheet samples of 0.118" thick, Plexiglas® MC 2069 Blue and Plexiglas® MC 2208 Yellow were each melt processed on a sheet extrusion line. These samples are commercially available from ATOFINA Chemicals, Inc. (Atoglas Division in North America). Samples of each of the 2 colors were cut to size (about 2"×2"). The sample edges were subsequently edge finished as described in Example 1.

Optical measurements were made on the individual samples as described in Example 1. The optical and color properties are summarized below in Table III.

TABLE III

Optical Properties of Monolithic Sheet Colors

| Sample | Thickness (inches) | Transmission (%) | Haze (%) | Transmitted Color | | |
|---|---|---|---|---|---|---|
| | | | | L* | a* | b* |
| 2069 Blue | 0.116 | 59.2 | 1.4 | 81.4 | −16.4 | −20.3 |
| 2208 Yellow | 0.120 | 79.5 | 1.6 | 91.5 | −12.9 | 109.2 |

The above Plexiglas® MC 2069 Blue and Plexiglas® MC 2208 Yellow samples were sandwiched together and then clamped to hold the layers together.

Example 4

Article of the Present Invention

An article was prepared as in Example 3 except that glycerol (same as described in Example 2) was applied to the mating surfaces of 2069 Blue and 2208 Yellow samples prior to sandwiching them together. The resultant 3-layer sample (2 layers of acrylic and 1 layer of glycerol) was then clamped together to minimize the thickness of the glycerol contact layer. The optical and color properties of the multi-layer samples from Examples 3 and 4 are summarized below in Table IV.

TABLE IV

Optical Properties of Multi-Layer Sheet Colors

| Sample | Thickness (inches) | Transmission (%) | Haze (%) | Transmitted Color | | |
|---|---|---|---|---|---|---|
| | | | | L* | a* | b* |
| Example 3 | 0.236 | 44.7 | 3.1 | 72.7 | −37.7 | 82.1 |
| Example 4 | 0.236 | 48.3 | 3.1 | 75.0 | −38.5 | 84.4 |

In Example 3, the transmission value is lower primarily due to the reflection losses at the acrylic/air/acrylic interfaces between the 2 acrylic layers. The glycerol was used in Example 4 to make optical contact between the acrylic layers and significantly reduce the above reflection losses, thus allowing a higher transmission value.

Additionally, when looking directly through the edge of the Example 3 sample (e.g. θ=0°), the blue surface layer and the yellow surface layer are each visible. The edge color of each layer is distinctly separate from the adjacent layer. As the viewing angle is incrementally increased to one approaching 90°, the edge color of each layer still remains separate from the color of the adjacent layer.

Furthermore, when looking directly through the edges of the Example 4 sample (e.g. θ=0°), the blue surface layer and the yellow surface layer are each visible and separate as in Example 3. However, as the viewing angle is incrementally increased, the edge colors of each of the layers change to a similar color (greenish) at a threshold viewing angle.

Example 5

Comparative

Monolithic sheet samples of 0.227" thick, Plexiglas® MC 3190 Fluorescent Green and 0.169" thick Plexiglas® MC 2025 Black were each melt processed on a sheet extrusion line. These samples are commercially available from ATOFINA Chemicals, Inc. (Atoglas Division in North America). Samples of each of the 2 colors were cut to size (about 3"×3"). The sample edges were subsequently edge finished as described in Example 1.

Optical measurements were made on the individual samples as described in Example 1. The optical and color properties are summarized below in Table V.

TABLE V

Optical Properties of Monolithic Sheet Colors

| Sample | Thickness (inches) | Transmission (%) | Haze (%) | Transmitted Color | | |
|---|---|---|---|---|---|---|
| | | | | L* | a* | b* |
| 3190 Green | 0.227 | 90.8 | 3.6 | 96.3 | −22.4 | 70.6 |
| 2025 Black | 0.169 | 0.0 | N/A | 0.0 | 0.0 | 0.0 |

The above Plexiglas® MC 3190 Green and Plexiglas® MC 2025 Black samples were sandwiched together and then clamped to hold the layers together.

Example 6

Article of the Present Invention

An article was prepared as in Example 5 except that glycerol (same as described in Example 2) was applied to the mating surfaces of 2025 Black and 3190 Green samples prior to sandwiching them together. The resultant 3-layer sample (2 layers of acrylic and 1 of glycerol) was then clamped together to minimize the thickness of the glycerol contact layer. The optical and color properties of the multi-layer samples from Examples 5 and 6 are summarized below in Table VI.

TABLE VI

Optical Properties of Multi-Layer Sheet Colors

| Sample | Thickness (inches) | Transmission (%) | Haze (%) | Transmitted Color L* | a* | b* |
|---|---|---|---|---|---|---|
| Example 5 | 0.396 | 0.0 | N/A | 0.0 | 0.0 | 0.0 |
| Example 6 | 0.396 | 0.0 | N/A | 0.0 | 0.0 | 0.0 |

In Examples 5 and 6, the transmission values are zero due to the presence of the 2025 Black opaque layer in each sample. The glycerol was used in Example 6 to make optical contact between the layers.

Additionally, when looking directly through the edge of the Example 5 sample (e.g. $\theta=0°$), the black surface layer and the yellow-green surface layer are each visible. The edge color of each layer is distinctly separate from the adjacent layer. As the viewing angle is incrementally increased to one approaching 90°, the edge color of the yellow-green layer still remains yellow-green and separate from the color of the adjacent black opaque layer.

Furthermore, when looking directly through the edges of the Example 6 sample (e.g. $\theta=0°$), the black surface layer and the yellow-green surface layer are each visible and separate as in Example 5. However, as the viewing angle is incrementally increased, the edge color of the yellow-green layer changes to a dark blackish-green color at a threshold viewing angle. The Example 6 sample exhibits an edgewise, angular multi-chromatic effect when viewing the light-transmitting acrylic layer of the 3-layer construction from the edges.

Example 7

Comparative

Monolithic sheet samples of 0.227" thick, Plexiglas® MC 3194 Fluorescent Yellow and 0.169" thick, Plexiglas® MC 2025 Black were melt processed on a sheet extrusion line. These samples are commercially available from ATOFINA Chemicals, Inc. (Atoglas Division in North America). Samples of each of the 2 colors were cut to size (about 3"×4"). The sample edges were subsequently edge finished as described in Example 1.

Optical measurements were made on the individual samples as described in Example 1. The optical and color properties are summarized below in Table VII.

TABLE VII

Optical Properties of Monolithic Sheet Colors

| Sample | Thickness (inches) | Transmission (%) | Haze (%) | Transmitted Color L* | a* | b* |
|---|---|---|---|---|---|---|
| 2025 Black-1 | 0.169 | 0.0 | N/A | 0.0 | 0.0 | 0.0 |
| 3194 Yellow | 0.227 | 90.5 | 3.7 | 96.2 | −17.8 | 57.4 |
| 2025 Black-2 | 0.169 | 0.0 | N/A | 0.0 | 0.0 | 0.0 |

The above Plexiglas® MC 3194 Yellow and Plexiglas® MC 2025 Black samples were sandwiched together and then clamped to hold the layers together.

Example 8

Article of the Present Invention

An article was prepared as in Example 7 except that glycerol (same as described in Example 2) was applied to the mating surfaces of 2025 Black and 3194 Yellow samples prior to sandwiching them together. The resultant 5-layer sample (3 layers of acrylic and 2 layers of glycerol) was then clamped together to minimize the thickness of each of the glycerol contact layers. The optical and color properties of the multi-layer samples from Examples 7 and 8 are summarized below in Table VIII.

TABLE VIII

Optical Properties of Multi-Layer Sheet Colors

| Sample | Thickness (inches) | Transmission (%) | Haze (%) | Transmitted Color L* | a* | b* |
|---|---|---|---|---|---|---|
| Example 7 | 0.565 | 0.0 | N/A | 0.0 | 0.0 | 0.0 |
| Example 8 | 0.566 | 0.0 | N/A | 0.0 | 0.0 | 0.0 |

In Examples 7 and 8, the transmission values are zero due to the presence of the 2025 Black opaque layers in each sample. The glycerol was used in Example 8 to make optical contact between the acrylic layers.

Additionally, when looking directly through the edge of the Example 7 sample (e.g. $\theta=0°$), the black surface layers and the yellow interlayer are each visible. The edge color of each layer is distinctly separate from the adjacent layer(s). As the viewing angle is incrementally increased to one approaching 90°, the edge color of the yellow layer still remains yellow and separate from the color of the adjacent black opaque layers.

Furthermore, when looking directly through the edges of the Example 8 sample (e.g. $\theta=0°$), the black surface layers and the yellow interlayer are each visible and separate as in Example 7. However, as the viewing angle is incrementally increased, the edge color of the yellow layer changes to a dark blackish-yellow color at a threshold viewing angle. The Example 8 sample exhibits an edgewise, angular multi-chromatic effect when viewing the light-transmitting acrylic layer of the 5-layer construction from the edges.

Example 9

Article of the Present Invention

Three-layer sheet samples of 0.219" total thickness were co-extruded on a sheet extrusion line. The 2 surface layers were fed from the same secondary extruder that was processing the resin formulation used to make Plexiglas® MC 3190 Fluorescent Green sheet. The interlayer was fed from the primary extruder that was processing the resin pellets used to produce the Plexiglas® MC 3152 Fluorescent Blue sheet. A co-extrusion setup was used whereby the melt stream from each of these extruders was fed to a feedblock/die assembly where the melts were layered and spread to the width of the die. The layered extrudate was subsequently polished between a series of polishing rolls to yield the resultant sheet thickness with a smooth, glossy finish on both sides. Samples of the resultant sheet were cut to size (about 2.5"×5"). The sample edges were subsequently edge finished as described in Example 1.

When looking directly through the edge of the Example 9 sample (e.g. $\theta=0°$), the thin, fluorescent yellow-green surface layers and the thick, fluorescent blue interlayer are each visible. The edge color of each layer is visibly different from the adjacent layer(s). However, as the viewing angle is incrementally increased, the edge colors of each of the layers changes to a greenish color at a threshold viewing angle. Note that the threshold viewing angle when viewing the edge through the 2.5" path length is greater than the threshold viewing angle observed when viewing the edge through the 5" path length.

Optical measurements were made on the co-extruded samples of Examples 9-11 as described in Example 1 and the properties are summarized below in Table IX.

TABLE IX

Optical Properties of Co-extruded Sheet Colors

| Sample | Thickness (inches) | Transmission (%) | Haze (%) | Transmitted Color |||
|---|---|---|---|---|---|---|
| | | | | L* | a* | b* |
| Example 9 | 0.219 | 90.0 | 1.5 | 96.0 | −2.9 | 4.4 |
| Example 10 | 0.354 | 67.0 | 5.4 | 85.5 | 26.4 | −2.9 |
| Example 11 | 0.360 | 79.0 | 97.4 | 91.2 | −1.8 | 0.8 |

Example 10

Article of the Present Invention

Two-layer sheet samples of 0.354" total thickness were co-extruded on a sheet extrusion line. The thinner surface layer was fed from the secondary extruder that was processing the resin formulation used to make Plexiglas® MC 3198 Fluorescent Red sheet. The thicker surface layer was fed from the primary extruder that was processing the resin pellets used to produce the Plexiglas® MC 3152 Fluorescent Blue sheet. The co-extrusion setup was the same as that described in Example 9. Samples of the resultant sheet were cut to size (about 4"×4"). The sample edges were subsequently edge finished as described in Example 1.

When looking directly through the edge of the Example 10 sample (e.g. $\theta=0°$), the thin, fluorescent red surface layer and the thick, fluorescent blue surface layer are each visible. The edge color of each layer is visibly different from the adjacent layer. However, as the viewing angle is incrementally increased, the edge colors of each of the layers changes to a pinkish color at a threshold viewing angle.

Example 11

Article of the Present Invention

Two-layer sheet samples of 0.360" total thickness were co-extruded on a sheet extrusion line. The thinner surface layer was fed from the secondary extruder that was processing a particle-containing resin formulation described below that contained the same colorant package as is used to make Plexiglas® MC 3194 Fluorescent Yellow sheet. The thicker surface layer was fed from the primary extruder that was processing the resin pellets used to produce the Plexiglas® MC 3152 Fluorescent Blue sheet. The co-extrusion setup was the same as that described in Example 9. The layered extrudate was subsequently polished between a series of polishing rolls to yield the resultant sheet thickness with a smooth, glossy finish on 1 side and a matte finish surface on the other side (due to the presence of the particles). Samples of the resultant sheet were cut to size (about 4"×4"). The sample edges were subsequently edge finished as described in Example 1.

The particle-containing feed stream for the above thin layer is described as follows.

Crosslinked particles comprised of primarily methyl methacrylate and styrene, that are substantially spherical, having a mean particle diameter of about 50 to 70 microns, and have a particle size distribution of between 10-110 microns in diameter, and a refractive index (nD) of 1.522 were melt blended into an acrylic molding resin (methyl methacrylate/ethyl acrylate 96/4) at 39% by weight. The refractive index (nD) of the acrylic molding resin used above was measured as 1.493 in conformance with ASTM D 542. The exact same colorant formulation and loading level used to make Plexiglas® MC 3194 Fluorescent Yellow sheet was also blended into the particle-containing resin.

When looking directly through the edge of the Example 11 sample (e.g. $\theta=0°$), the thin, fluorescent yellow surface layer and the thick, fluorescent blue surface layer are each visible. The edge color of each layer is visibly different from the adjacent layer. However, as the viewing angle is incrementally increased, the edge colors of each of the layers changes to a greenish color at a threshold viewing angle.

Example 12

Article of the Present Invention

A sample of the co-extruded sheet described in Example 9 was cut into a trapezoidal shape 5" long. At one end of the 5" dimension, the sample width was 1" whereas at the other end it was 2.5". The sample edges were subsequently edge finished as described in Example 1.

When looking directly through the edge of the Example 12 sample (e.g. $\theta=0°$), the thin, fluorescent yellow-green surface layer and the thick, fluorescent blue surface layer are each visible. The edge color of each layer is visibly different from the adjacent layer. However, as the viewing angle is incrementally increased, the edge colors of each of the layers changes to a greenish color at a range of threshold viewing angles that is dependent on the path length of the edge the sample is being viewed through. By placing the trapezoidal shape such that the viewing path length may change from 1" to 2.5" along the edge, the smallest threshold viewing angle is observed at the 2.5" path length and the largest threshold viewing angle is observed at the 1" path length. Consequently, the edge colors may be different along the sample edge due to the different threshold angles achievable.

Example 13

Article of the Present Invention

These articles were prepared as in Examples 1 and 2 except that water was applied to each side of the 3190 Green sample prior to sandwiching it between the 3152 Blue samples. The refractive index of water is 1.333. The resultant 5-layer sample (3 layers of acrylic plus 2 layers of water) was then clamped together to minimize the thickness of each of the water contact layers. The optical and color properties of the multi-layer samples from Examples 1, 2 and 13 are summarized below in Table X.

TABLE X

Optical Properties of Multi-Layer Fluorescent Sheet Colors

| Sample | Thickness (inches) | Transmission (%) | Haze (%) | Transmitted Color |||
|---|---|---|---|---|---|---|
| | | | | L* | a* | b* |
| Example 1 | 0.354 | 76.3 | 4.2 | 90.0 | −15.6 | 39.9 |
| Example 2 | 0.355 | 88.0 | 2.7 | 95.2 | −16.6 | 42.2 |
| Example 13 | 0.355 | 87.0 | 3.8 | 94.7 | −16.7 | 41.8 |

The transmission value of Example 13 lies between Examples 1 and 2 due primarily to the reflection losses at the acrylic/water/acrylic interfaces. Water was used in Example 13 to make optical contact between the layers. Since the refractive index of water (1.333) is closer to that of the Plexiglas® MC sheet (1.492) than the refractive index of air (1.000) is to the acrylic sheet, the reflection losses are decreased compared to Example 1. In contrast, since the refractive index of water (1.333) is not as close to that of the Plexiglas® MC sheet (1.492) as the refractive index of glycerol (1.473) is to the acrylic sheet, the reflection losses between the acrylic layers are slightly increased compared to Example 13. Therefore, an intermediate transmission value is achieved in the 5-layer sample of Example 13.

Additionally, it was noted in the descriptions of Example 2, that when looking directly through the edges of the Example 2 sample (e.g. $\theta=0°$), the 2 blue surface layers and the yellow-green middle layer are each visible and separate as in Example 1. However, as the viewing angle is incrementally increased, the edge colors of each of the layers change to a similar color (greenish—with color contributions from each of the 3 light-transmitting acrylic layers) at a threshold viewing angle. This was in contrast to Example 1 where the three principle colors remained visible at any angle.

Furthermore, when looking directly through the edges of Example 13 sample (e.g. $\theta=0°$), the 2 blue surface layers and the yellow-green middle layer are each visible and separate as in Examples 1 and 2. As the viewing angle is incrementally increased, the edge colors of each of the layers change to a similar color (greenish) at a threshold viewing angle as in Example 2. However, it is noted that the threshold viewing angle for Example 13 is significantly larger than the threshold viewing angle for Example 2. It was also noted that the threshold viewing angle is about the same when viewing through the 3" or 4" path lengths.

Example 14

Comparative

Samples (about 2"×3") of 0.227" thick, Plexiglas® MC 3193 Fluorescent Yellow-Orange and 0.229" thick, colorless Tuffak® XL polycarbonate were each cut from the respective melt processed sheets. These sheet products are commercially available from ATOFINA Chemicals, Inc. (Atoglas Division in North America). The edges of the Plexiglas® MC sample were subsequently edge finished as described in Example 1. The edges of the Tuffak® XL sample were buffed and polished to remove saw-cut marks.

Optical measurements were made on the individual samples as described in Example 1. The optical and color properties are summarized below in Table XIV.

Note that the Tuffak XL is a co-extruded sheet product. It is comprised of 2 colorless layers: a polycarbonate substrate and a thin UV-protective surface layer. This UV-protective layer is thin and essentially invisible to the naked eye. For the purposes of these examples, the 2 layers will be considered as one "combined polycarbonate layer." In both Examples 14 and 15, the UV-protective layer was facing to the outside. Color and Haze measurements were made with the UV-protective layer facing away from the light source. Also note that the manufacturer reports a refractive index value of 1.586 for the polycarbonate sheet.

TABLE XIV

Optical Properties of Acrylic and Polycarbonate Sheet Products

| Sample | Thickness (inches) | Transmission (%) | Haze (%) | Transmitted Color | | |
|---|---|---|---|---|---|---|
| | | | | L* | a* | b* |
| Plexiglas ® MC | 0.227 | 70.9 | 5.38 | 87.4 | 20.8 | 35.5 |
| Tuffak ® XL | 0.229 | 83.8 | 2.92 | 93.4 | −0.8 | 0.6 |

The above Plexiglas® MC 3193 Yellow-Orange and colorless Tuffak® XL polycarbonate samples were sandwiched together and then clamped to hold the layers together.

Example 15

Article of the Present Invention

The same as Example 14 except that glycerol (same as described in Example 2) was applied to the mating surfaces of the Plexiglas® MC and Tuffak® XL samples prior to sandwiching them together. The resultant 3-layer sample (1 layer of acrylic, 1 layer of glycerol, and 1 combined layer of polycarbonate) was then clamped together to minimize the thickness of the glycerol contact layer. The optical and color properties of the multi-layer samples from Examples 14 and 15 are summarized below in Table XV.

TABLE XV

Optical Properties of Multi-Layer Sheet Colors

| Sample | Thickness (inches) | Transmission (%) | Haze (%) | Transmitted Color | | |
|---|---|---|---|---|---|---|
| | | | | L* | a* | b* |
| Example 14 | 0.456 | 59.7 | 7.44 | 81.7 | 19.0 | 34.9 |
| Example 15 | 0.457 | 64.2 | 6.98 | 84.1 | 19.7 | 35.6 |

In Example 14, the transmission value is lower primarily due to the reflection losses at the acrylic/air/polycarbonate interfaces between the 2 plastic samples. The glycerol was used in Example 15 to make optical contact between the acrylic and polycarbonate layers. This significantly reduced the above reflection losses, thus allowing a higher transmission value compared to Example 14.

Additionally, when looking directly through the edge of the Example 14 sample (e.g. $\theta=0°$), the yellow-orange acrylic layer and the combined polycarbonate layers are each visible. The edge color of each layer is distinctly separate from the adjacent layer. As the viewing angle is incrementally increased to one approaching 90°, the edge color of each layer still remains separate from the color of the adjacent layer.

Furthermore, when looking directly through the edges of the Example 15 sample (e.g. $\theta=0°$), the yellow-orange acrylic layer and the combined polycarbonate layers are each visible and separate as in Example 14. However, as the viewing angle is incrementally increased, the edge color of the combined polycarbonate layers change to a color similar to that of the yellow-orange acrylic layer at a threshold viewing angle.

Example 16

Comparative

Monolithic samples (about 2"×3") of 0.227" thick, Plexiglas® MC 3193 Fluorescent Yellow-Orange and colorless Vivak® PETG (Polyethylene Terephthalate-Glycol modified) were each cut from the respective melt processed sheets. The Plexiglas® MC sheet is commercially available from ATOFINA Chemicals, Inc. (Atoglas Division in North America). The PETG sheet is commercially available from Sheffield Plastics Inc. (A Bayer Polymers Company). The edges of the Plexiglas® MC sample were subsequently edge finished as described in Example 1. The edges of the PETG sample were buffed and polished to remove saw-cut marks.

Optical measurements were made on the individual samples as described in Example 1. The optical and color properties are summarized below in Table XVI. Note that the manufacturer reports a refractive index value of 1.57 for PETG sheet.

TABLE XVI

Optical Properties of Monolithic Sheet Colors

| Sample | Thickness (inches) | Transmission (%) | Haze (%) | Transmitted Color | | |
|---|---|---|---|---|---|---|
| | | | | L* | a* | b* |
| Plexiglas ® MC | 0.227 | 70.9 | 5.87 | 87.4 | 20.8 | 35.5 |
| PETG | 0.223 | 83.3 | 1.36 | 93.1 | 0.5 | 0.7 |

The above Plexiglas® MC 3193 Yellow-Orange and colorless PETG samples were sandwiched together and then clamped to hold the layers together.

Example 17

Article of the Present Invention

The same as Example 16 except that glycerol (same as described in Example 2) was applied to the mating surfaces of the Plexiglas® MC and PETG samples prior to sandwiching them together. The resultant 3-layer sample (1 layer of acrylic, 1 layer of glycerol, and one layer of PETG) was then clamped together to minimize the thickness of the glycerol contact layer. The optical and color properties of the multi-layer samples from Examples 15 and 16 are summarized below in Table XVII.

TABLE XVII

Optical Properties of Multi-Layer Sheet Colors

| Sample | Thickness (inches) | Transmission (%) | Haze (%) | Transmitted Color | | |
|---|---|---|---|---|---|---|
| | | | | L* | a* | b* |
| Example 16 | 0.451 | 59.5 | 6.65 | 81.6 | 20.0 | 34.6 |
| Example 17 | 0.452 | 64.4 | 5.31 | 84.2 | 20.5 | 35.0 |

In Example 16, the transmission value is lower primarily due to the reflection losses at the acrylic/air/PETG interfaces between the 2 plastic layers. The glycerol was used in Example 17 to make optical contact between the acrylic and PETG layers. This significantly reduced the above reflection losses, thus allowing a higher transmission value compared to Example 16.

Additionally, when looking directly through the edge of the Example 16 sample (e.g. θ=0°), the yellow-orange acrylic layer and the PETG layer are each visible. The edge color of each layer is distinctly separate from the adjacent layer. As the viewing angle is incrementally increased to one approaching 90°, the edge color of each layer still remains separate from the color of the adjacent layer.

Furthermore, when looking directly through the edges of the Example 17 sample (e.g. θ=0°), the yellow-orange acrylic layer and the PETG layer are each visible and separate as in Example 16. However, as the viewing angle is incrementally increased, the edge color of the PETG layer changes to a color similar to that of the yellow-orange acrylic layer at a threshold viewing angle.

Example 18

Comparative

A monolithic sample (about 2"×2") of 0.227" thick, Plexiglas® MC 3193 Fluorescent Yellow-orange was cut from the sheet. This sheet product is commercially available from ATOFINA Chemicals, Inc. (Atoglas Division in North America). The sample edges were subsequently edge finished as described in Example 1. A sample of commercially available 0.080" thick, colorless, anti-reflective non-glare glass was obtained from a local picture frame supply retailer that cut the sample to size (about 4"×4") and finished the edges.

Optical measurements were made on the individual samples as described in Example 1. The optical and color properties are summarized below in Table XVIII.

TABLE XVIII

Optical Properties of Monolithic Sheet Colors

| Sample | Thickness (inches) | Transmission (%) | Haze (%) | Transmitted Color | | |
|---|---|---|---|---|---|---|
| | | | | L* | a* | b* |
| Plexiglas ® MC | 0.227 | 70.9 | 5.63 | 87.4 | 20.8 | 35.5 |
| Glass | 0.080 | 89.8 | 1.62 | 95.9 | −0.7 | 0.1 |

The above Plexiglas® MC 3193 Yellow-Orange and the glass samples were sandwiched together with the Plexiglas® MC placed on the side of the glass opposite the non-glare coating. The smaller Plexiglas® MC sample was placed at one corner of the larger glass sample such that two edges of the Plexiglas® MC sample were flush with part of the two edges of the glass sample. The remaining two edges of the Plexiglas® MC were not flush with the glass sample.

Example 19

Article of the Present Invention

The same as Example 18 except that glycerol (same as described in Example 2) was applied to the mating surfaces of the Plexiglas® MC and glass samples prior to sandwiching them together. The resultant 3-layer sample (1 layer of acrylic, 1 layer of glycerol, and one layer of glass) was then clamped together to minimize the thickness of the glycerol contact layer. The optical and color properties of the multi-layer samples from Examples 18 and 19 are summarized below in Table XIX.

TABLE XIX

Optical Properties of Multi-Layer Sheet Colors

| Sample | Thickness (inches) | Transmission (%) | Haze (%) | Transmitted Color | | |
|---|---|---|---|---|---|---|
| | | | | L* | a* | b* |
| Example 18 | 0.307 | 64.1 | 7.11 | 84.0 | 19.3 | 34.6 |
| Example 19 | 0.308 | 68.5 | 6.71 | 86.3 | 20.5 | 34.6 |

In Example 18, the transmission value is lower primarily due to the reflection losses at the acrylic/air/glass interfaces between the Plexiglas® MC and glass layers. The glycerol was used in Example 19 to make optical contact between the acrylic and glass layers. This significantly reduced the above reflection losses, thus allowing a higher transmission value compared to Example 18.

Additionally, when looking directly through any edge of either the Plexiglas or glass layer of the Example 18 sample (e.g. θ=0°), the yellow-orange acrylic layer and the glass layer are each visible. The edge color of each layer is distinctly separate from the adjacent layer. As the viewing angle is incrementally increased to one approaching 90°, the edge color of each layer still remains separate from the color of the adjacent layer.

Furthermore, when looking directly through any edge of the Example 19 sample (e.g. θ=0°), the yellow-orange acrylic layer and the glass layer are each visible and separate as in Example 18. However, as the viewing angle is incrementally increased, the edge color of a segment of each of the glass layer's four edges changes to a color similar to that of the yellow-orange acrylic layer at a threshold viewing angle as long as some portion of the viewing length behind that segment of the glass edge is in optical contact with the acrylic sample.

It is noted that a threshold viewing angle is visible in each edge of the larger glass sample, even those that are not flush with an acrylic edge, provided that a portion of the viewing length behind the glass edge is in optical contact with the acrylic sample. Note that if a glass edge is viewed such that the acrylic is not in optical contact for a portion of the viewing length behind the glass edge, the edge color of the glass does not change.

Example 20

Article of the Present Invention

Two-layer sheet samples of 0.212" total thickness were co-extruded on a sheet extrusion line. The thinner surface layer was fed from the same secondary extruder that was processing the resin formulation used to make Plexiglas® MC 3152 Fluorescent Blue sheet. The thicker surface layer was fed from the primary extruder that was processing the resin pellets used to produce the Plexiglas® MC 3120 Blue sheet. A co-extrusion setup was used whereby the melt stream from each of these extruders was fed to a feedblock/die assembly where the melts were layered and spread to the width of the die. The layered extrudate was subsequently polished between a series of polishing rolls to yield the resultant sheet thickness with a smooth, glossy finish on both sides. Samples of the resultant sheet were cut to size (about 4"×5"). The sample edges were subsequently edge finished as described in Example 1.

When looking directly through the edge of the Example 20 sample (e.g. θ=0°), the thin, fluorescent blue surface layer and the thick, transparent blue surface layer are each visible. The edge color of each layer is visibly different from the adjacent layer. However, as the viewing angle is incrementally increased, the edge colors of each of the layers changes to a bluish color at a threshold viewing angle. Note that the threshold viewing angle when viewing the edge through the 4" path length is greater than the threshold viewing angle observed when viewing the edge through the 5" path length.

Optical measurements were made on the co-extruded samples of Examples 20 and 21 as described in Example 1 and the properties are summarized below in Table XX.

TABLE XX

Optical Properties of Co-extruded Sheet Colors

| Sample | Thickness (inches) | Transmission (%) | Haze (%) | Transmitted Color | | |
|---|---|---|---|---|---|---|
| | | | | L* | a* | b* |
| Example 20 | 0.212 | 91.9 | 0.58 | 96.0 | −0.6 | −2.4 |
| Example 21 | 0.210 | 82.5 | 98.4 | 92.6 | 0.2 | −3.3 |

Example 21

Article of the Present Invention

Two-layer sheet samples of 0.210" total thickness were co-extruded on a sheet extrusion line. The thinner surface layer was fed from the secondary extruder that was processing a particle-containing resin formulation described below that contained the same colorant package as is used to make Plexiglas® MC 3152 Fluorescent Blue sheet. The thicker surface layer was fed from the primary extruder that was processing the resin pellets used to produce the Plexiglas® MC 3120 Blue sheet. The co-extrusion setup was the same as that described in Example 20. The layered extrudate was subsequently polished between a series of polishing rolls to yield the resultant sheet thickness with a smooth, glossy finish on 1 side and a matte finish surface on the other side (due to the presence of the particles). Samples of the resultant sheet were cut to size (about 4"×5"). The sample edges were subsequently edge finished as described in Example 1.

The particle-containing feed stream for the above thin layer is the same as the one described in Example 11 except for the colorants. In this Example, the exact same colorant formulation and loading level used to make Plexiglas® MC 3152 Fluorescent Blue sheet was also blended into the particle-containing resin.

When looking directly through the edge of the Example 21 sample (e.g. θ=0°), the thin, fluorescent blue surface layer and the thick, transparent blue surface layer are each visible. The edge color of each layer is visibly different from the adjacent layer. However, as the viewing angle is incrementally increased, the edge colors of each of the layers changes to a bluish color at a threshold viewing angle.

While the foregoing has described what are considered to be preferred embodiments of the invention it is understood that various modifications may be made therein and that the invention may be implemented in various forms and embodiments, and that it may be applied in numerous applications, only some of which have been described herein. It is intended by the following claims to claim all modifications and variations which fall within the true scope of the invention.

What is claimed is:

1. An article comprising two or more layers in optical contact, each of said layers having a principal color, wherein one or more of said layers is light transmitting, said article having at least one edge exposing at least one light transmitting layer, wherein the observed color of said at least one exposed light transmitting layer, when viewed along said edge, appears different than its principal color (shows angular multichromatic characteristics) solely due to the viewing angle, and wherein each layer of said article has a thickness of from greater than 0.1 to 100 mm, wherein at least one light transmitting layer has a thickness of from 1 to 100 mm.

2. The article of claim 1 wherein the observed color of said at least one exposed light transmitting layer, when viewed along said edge, changes at one or more threshold viewing angles.

3. The article of claim 1 wherein the observed color of said at least one exposed light transmitting layer, when viewed along said edge, appears to be a mix of two or more principal colors.

4. The article of claim 1 comprising three or more layers.

5. The article of claim 1 comprising two or more layers that are light transmitting.

6. The article of claim 1 wherein all of said layers are light transmitting.

7. The article of claim 1 wherein at least one of said layers is opaque or translucent.

8. The article of claim 1 wherein said two or more layers comprise plastic or glass.

9. The article of claim 8 wherein said two or more layers comprise acrylic polymer.

10. The article of claim 9 wherein said acrylic polymer comprises polymethyl methacrylate.

11. The article of claim 1 wherein said two or more layers are made of the same material.

12. The article of claim 1 having at least two adjacent light transmitting layers.

13. The article of claim 1 wherein the difference between indices of refraction of adjacent layers is 0.1 or less.

14. The article of claim 1 wherein the indices of refraction of adjacent layers are within about 0.5 of each other.

15. The article of claim 1 wherein said layers have indices of refraction greater than air.

16. The article of claim 1 wherein said layers have an index of refraction of at least about 1.05.

17. The article of claim 1 having a depth measured from said edge wherein said depth is variable.

18. The article of claim 17 wherein said depth is varied by cuts through said layers.

19. The article of claim 1 wherein said article is produced by coextrusion or fusion bonding of said layers.

20. The article of claim 1 comprising interlayer material.

21. The article of claim 20 wherein said interlayer material is a liquid having an index of refraction between about 1.05 and about 2.0.

22. The article of claim 1 wherein said two or more layers are light transmitting acrylic polymer having indices of refraction of at least about 1.05 and within about 0.5 of each other, wherein said two or more layers are coextruded.

23. The article of claim 1 wherein said two or more layers are light transmitting acrylic polymer having indices of refraction of at least about 1.05 and within about 0.5 of each other, wherein said two or more layers are separated by an interlayer having a lower index of refraction than said two or more layers.

24. The article of claim 23 wherein said interlayer is a liquid.

25. The article of claim 23 wherein the index of refraction of said interlayer is lower by about 0.1 or less.

26. The article of claim 1 wherein said article is a sheet.

27. The article of claim 26 wherein said sheet is transformed into a three-dimensional form.

28. The article of claim 26 wherein said sheet is transformed into three-dimensional form suitable for a display, consumer product, or decorative support for an object.

29. The article of claim 1 in the form of a display, consumer product, or decorative support for an object.

30. The article of claim 1 wherein said article further has a fluorescent, phosphorescent, electrochromic, photochromic, pearlescent, or effervescent visual effect.

31. The article of claim 1 wherein each layer of said article has a thickness 1 mm to 100 mm.

\* \* \* \* \*